United States Patent [19]

Robinson

[11] 4,252,026

[45] Feb. 24, 1981

[54] MULTIPLE LINE OF SIGHT ULTRASONIC APPARATUS

[75] Inventor: David E. Robinson, Bilgola Plateau, Australia

[73] Assignee: The Commonwealth of Australia, C/-The Department of Health, Phillip, Australia

[21] Appl. No.: 3,483

[22] Filed: Jan. 15, 1979

Related U.S. Application Data

[63] Continuation of Ser. No. 758,047, Jan. 10, 1977, abandoned, which is a continuation-in-part of Ser. No. 561,595, Mar. 24, 1975, abandoned.

[51] Int. Cl.³ .......................................... G01N 29/00
[52] U.S. Cl. .................................. 73/626; 128/660
[58] Field of Search .......................... 128/660–663; 73/626; 358/112

[56] References Cited

U.S. PATENT DOCUMENTS

| | | | |
|---|---|---|---|
| 3,163,784 | 12/1964 | Renaut | 73/62 E |
| 3,561,430 | 2/1971 | Filler | 128/661 |
| 3,587,561 | 6/1971 | Ziedonis | 128/661 |
| 3,675,472 | 7/1972 | Kay et al. | 367/105 |
| 3,778,757 | 12/1973 | Houston et al. | 73/626 |
| 3,789,833 | 2/1974 | Bom | 128/660 |
| 3,805,596 | 4/1974 | Klahr | 128/661 |
| 3,820,387 | 6/1974 | Grabendorfer et al. | 73/626 |
| 3,881,466 | 5/1975 | Wilcox | 128/661 |
| 3,895,381 | 7/1975 | Kock | 340/5 MP |
| 3,895,525 | 7/1975 | Eichelberger et al. | 73/612 |
| 3,911,730 | 10/1975 | Niklas | 73/626 |
| 3,919,683 | 11/1975 | Itamura et al. | 340/1 R |
| 3,936,791 | 2/1976 | Kossoff | 73/626 |
| 3,950,723 | 4/1976 | Gilmour | 367/123 |
| 3,967,233 | 6/1976 | Maguer et al. | 367/105 |
| 3,979,711 | 9/1976 | Maginess et al. | 73/626 |
| 4,005,258 | 1/1977 | Dory | 358/112 |
| 4,023,175 | 5/1977 | Brown et al. | 367/105 |
| 4,159,462 | 6/1979 | Rocha et al. | 128/661 |

*Primary Examiner*—Robert W. Michell
*Assistant Examiner*—Francis J. Jaworski

[57] ABSTRACT

An apparatus for pulse-echo ultrasonic examination, particularly in medical diagnostic examination comprised of one or more transducer elements for transmitting divergent pulses of ultrasonic energy into the object under examination and a greater number of transducer elements providing a plurality of received beams for each pulse transmitted.

7 Claims, 4 Drawing Figures

MULTIPLE LINE OF SIGHT ULTRASONIC APPARATUS

CROSS-REFERENCE TO RELATED APPLICATION

This is a continuation of application Ser. No. 758,047, filed 1/10/77, now abandoned, which is a Continuation-In-Part of applicant's U.S. patent appln. No. 561,595, filed Mar. 24, 1975, now abandoned.

This invention relates to the technique of ultrasonic echoscopy of objects and in particular to an extension of known techniques of ultrasonic echoscopy to provide more useful information concerning the examined objects. It is particularly, but not solely, directed to the more effective acquisition of data in medical diagnosis utilising this technique.

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically in the 1–30 MHz frequency range, along a line called the beam axis into the examined object where any acoustic impedance discontinuities in the object reflect and return some of the energy along the same beam axis in the form of an echo. This echo is received, converted into an electric signal and displayed as an echogram on a cathode ray oscilloscope, a film, a chart or the like.

The echogram may constitute either a one dimensional or a two dimensional representation and in both cases the information is contained in the position and magnitude of the echo displayed. In a one dimensional display, the position along a base line is used to indicate the distance to the reflecting surface whilst the magnitude of the echo is displayed, for example, as a deflection of the base line or as an intensity change. In a two dimensional display, the position along a base line is used to indicate the distance to the reflecting surface as in a one dimensional display, and the direction of the base line is used to represent the direction of propagation of the acoustic energy which is the beam axis. The two dimensional display is obtained by changing this direction of propagation of the acoustic energy and by instituting a similar but not necessarily identical movement of the base line of the display. The magnitude of the echo is displayed as for a one dimensional display; for example, as a deflection of the base line or as an intensity change.

The technique of ultrasonic echoscopy is used in medical diagnosis to obtain information about the anatomy of patients. The application of this technique is now widely investigated and is described, for example, by D. E. Robinson in Proceeding of the Institution of Radio and Electronics Engineers Australia, Vol. 31. No. 11, pages 385–392, November, 1970: "The Application of Ultrasound In Medical Diagnosis". As pointed out in this article, ultrasonic echoscopy may be used to produce displays resembling anatomical cross-sections which have proved clinically useful when the desired information concerns physical dimensions, shapes of organs or structures or the like. Ultrasonic echography has proved of particular value as a diagnostic aid in the abdomen and pregnant uterus, eye, breast, brain, lung, kidney, liver and heart, these being areas of soft tissue with little bone and air. In general, the technique is considered to complement other techniques to provide a more complete picture of the patients condition, however particularly in pregnancies, ultrasonic echoscopy may be useful in place of X-rays where the latter may not give sufficient information or may be dangerous. In medical use, a pulse of ultrasonic energy is transmitted into a patient in a known direction and echoes are received from reflecting surfaces within the body. The time delay between a transmitted pulse and the received echo depends on the distance from the transmitter to the reflecting surface and the distance information so obtained may be displayed in a suitable way for interpretation and clinical use as a one dimensional range reading or as a two dimensional cross section as previously described.

This known system suffers from a disadvantage due to the time required to obtain a cross-sectional picture. The cross-sectional picture is made up of a multiplicity of lines of information corresponding to each beam axis position at which a pulse was transmitted and echoes received. The time required to obtain each line of information is fixed by the depth of the tissues of interest and the velocity of propagation of sound in the tissues to be examined. For a particular area of interest neither of these parameters is under the control of the operator and they form a basic limitation on the time required to obtain an echogram.

In U.S. Pat. No. 3,789,833 to Bom, there is disclosed the formation of an array of transducer elements arranged in a line, each providing a separate ultrasonic line of sight. Each array element is pulsed in turn, returned echoes are received and displayed on a screen and then another array element is pulsed. The time required to form each displayed image is $2 \times D \times N/v$ where D is the required depth of penetration, v is the velocity of propagation and N is the number of lines required. Thus, for a 64 line cross-sectional display with 20 cm penetration in tissue having a velocity of propagation of 1540 m/s, 16.7 msec are required to obtain a complete picture. Thus the rate of obtaining pictures is approximately sixty times per second which may be insufficient for some diagnostic situations such as the visualisation of the heart. Of course, increasing the number of lines of the depth of penetration increases the time required to form a complete picture and decreases the number of pictures per second which can be obtained. One prime limitation of the system disclosed by Bom is that the line spacing fixes the size of the transducer elements and the resulting ultrasonic resolution. U.S. Pat. No. 3,881,466 to Wilcox discloses the use of a plurality of transducer elements to form each ultrasonic beam, thus breaking the link between line spacing and resolution, and it is also known to apply time delays to signals associated with the various elements of a transducer element array in forming the ultrasonic beam, to cause a focusing action within the plane of scan. In all cases, however, the minimum time requirement in formation of a complete picture is limited as has been described above.

It is a primary object of the present invention to provide an improved apparatus and method for the ultrasonic echoscopic examination whereby the time required to obtain each cross-sectional picture is reduced allowing the examination of moving structures with greater clarity while retaining all the above described improvements in resolution and accuracy.

According to this invention, there is provided apparatus for the ultrasonic examination of an object comprising a linear array of discrete transducer elements;

means to energize at least one element of said array to transmit pulses of ultrasonic energy into the object in the form of a diverging beam of transmitted energy which ensonifies a region within the object; and means for receiving echoes of said pulses of ultrasonic energy reflected by acoustic impedance discontinuities within said region of the object, said means for receiving echoes comprising means to activate said transducer elements to receive echoes of each transmitted pulse along a plurality of received beams.

Preferably, the means for receiving echoes comprises a plurality of said transducer elements arranged to provide a plurality of received beams with beam axes corresponding to each position required for a line of information on a resulting cross-sectional visualisation of the object; and said means for transmitting pulses comprises a number of said transducer elements less in number than the number of received beams and arranged to provide said diverging beam of transmitted energy to ensonify the region within the object covered by the plurality of received beams.

In another aspect, said means for transmitting pulses comprises a single element of said array and said means for receiving echoes comprises a plurality of groups of elements of said array providing said plurality of received beams, and further including means for repeatedly sampling the echo information of each of said received beams during the period while echoes are being received.

In another aspect, this invention provides a method of ultrasonic examination of an object comprising the steps of transmitting pulses of ultrasonic energy into the object by energizing at least one element of a linear array of discrete transducer elements to form a diverging beam of transmitted energy which ensonifies a region within the object; and receiving echoes of said pulses of ultrasonic energy reflected by acoustic impedance discontinuities within the object by activating a plurality of said transducer elements to receive echoes of each transmitted pulse along a plurality of received beams.

In order to display the echo information from each received beam axis, the beam selector switch switches rapidly from one beam forming circuit to the next many times during the period in which echoes are returning and the deflected spot on the display is caused to move likewise. In this way a plurality of lines of echo data are received for each pulse transmitted and hence the absolute minimum time required for a cross-sectional picture is reduced, with a proportionally greater reduction as the number of beam axis positions used for each transmitted pulse is increased. By this technique, the time required for formation of a complete picture is $2 \times D \times N/(v \times M)$, where D, N and v are as previously defined, and M is the number of beams received and displayed from a single transmitted pulse. Typically, M could be 6 and the rate of obtaining complete pictures with the same number of lines per picture would thus be increased by a factor of 6 without adversely affecting display quality. The apparatus of the present invention thus also includes display means including switch means for operating the display means to display echo information from the received beams.

The electrical and mechanical structure necessary to implement the invention are well known in the art, and it should be understood that applicant's invention lies in the novel concept of arranging such known parts to produce a new result. In this respect, reference is made to U.S. Pat. Nos. 3,166,731 and 3,086,195 as showing electronic scanning and focusing arrangements. In view of the detailed disclosure of the electronics and structure of these prior arrangements, no detailed discussion of the various electronic and mechanical structures need be made herein.

One embodiment of the invention is illustrated in the accompanying drawings in which.

Figure 1:
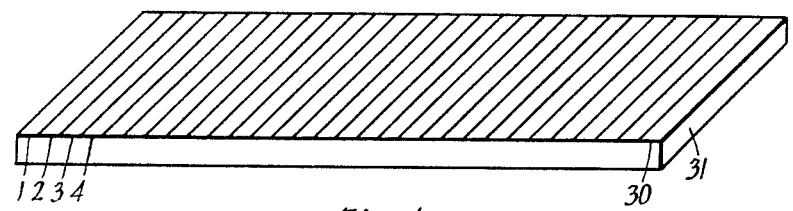
FIG. 1 illustrates an arrangement of transducer elements which may be used in accordance with this invention.
Figure 2:
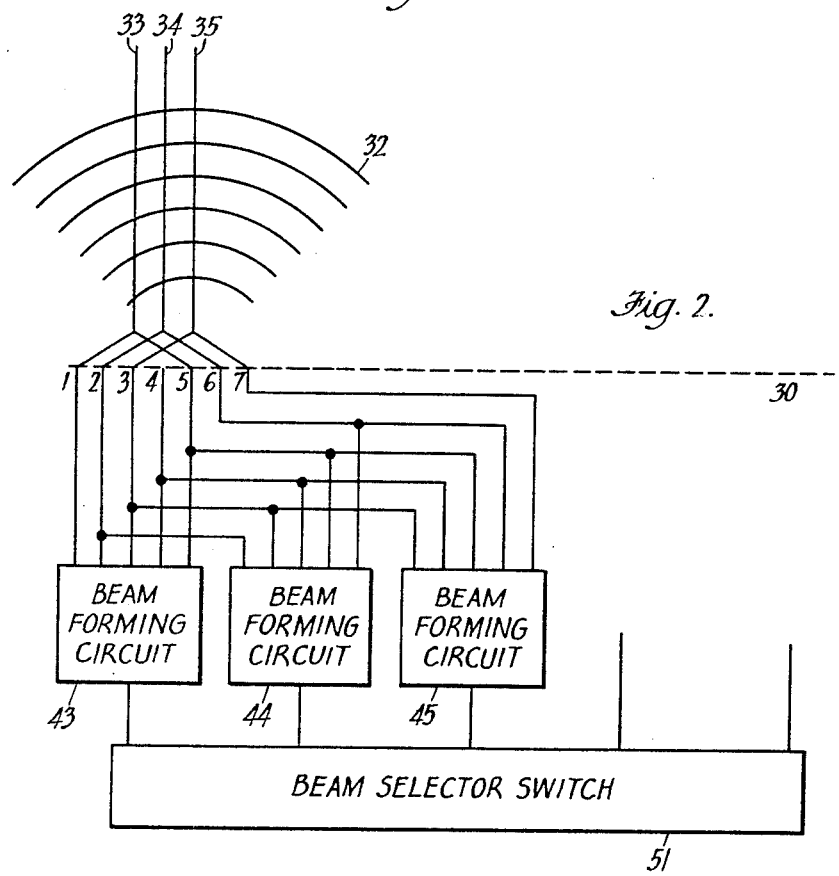
FIG. 2 shows the transmitted and received beams and the processing system utilising the principles of the present invention.

The transducer array depicted in FIG. 1 consists of a plurality of active transducer elements, and by way of example thirty rectangular elements 1–30 are shown mounted on the flat rectangular strip 31. The width of each rectangular element is made equal to the actual spacing required between received beams. This will normally be sufficiently small with respect to the wavelength that the transmitted pulse beam diverges to ensonify the region above a number of receiver elements. For example, referring to FIG. 2, assume that element 5 is used to transmit as shown in FIG. 2 and its beam 32 ensonifies the region above elements 1 to 10. To obtain a narrow received beam a plurality of transducer elements may be used together with appropriate time delays being utilised to obtain focusing, for example using elements 1–5 beam 33 may be formed with its axis above element 3; similarly using elements 2–6 a beam 34 may be formed above element 4 and so on.

Figure 3:
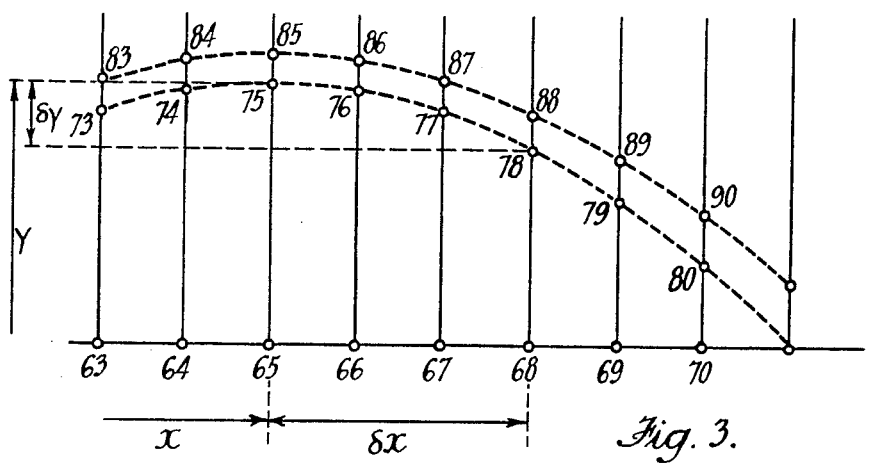
FIG. 3 illustrates a method of echo display in accordance with this invention.

The display of FIG. 3 is generated by knowledge of the values x, y, δx shown on the Figure. The value x is given by the distance along the transducer to the centre of the transmitting transducer element. The value y is given by a constant multiplied by time and represents the depth into the examined object. The value δx is the offset from the centre of the transmitting transducer element to the centre of the formed received beam. This display is more complex than displays obtained by the prior art methods because it comprises a display of a plurality of received beams concurrently. Thus the displayed point must traverse a curve or locus across all the received beams at a similar time delay of received echo before going onto greater time delays and thus greater ranges. The curve 73-75-80 represents the position of reflectors which give rise to echoes at constant time delay. Thus the path lengths 65-73-63, 65-75-65, 65-80-70 are all equal. The direct path length 65-75-65 given by 2y must equal any inclined path length such as 65-78-68 which is given by $$\sqrt{(\delta x)^2 + (y-\delta y)^2} + (y-\delta y); \text{ i.e.,}$$
$$2y = \sqrt{(\delta x)^2 + (y-\delta y)^2} + y - \delta y.$$

From this relationship the required value for δy can be found to be $$\delta y = \delta x^2/4y.$$

Also shown in FIG. 2 is a scheme for processing the returned echo data in which beam forming circuits 43, 44 45 produce signals representing echoes received along beams in beamaxis positions 33, 34, 35 etc. respectively and these are fed to the beam selector switch 51. During the time the echoes are returning, the beam selector 51 and the position of the dot on the display screen are switched rapidly to obtain and display all the data. For instance FIG. 3 shows a diagram of a number of positions 73–80 on a number of beams from which echoes return at the same delay time, the said positions lying on a parabolic curve. Each of the said beams must be sampled and the results displayed during the time available until echoes are returning from the next set of sample points 83–90. Therefore in this case a complete set of information on eight beam axis positions is obtained for one transmitted pulse. The procedure is then repeated using another transmitting element, such as 7.

Figure 4:
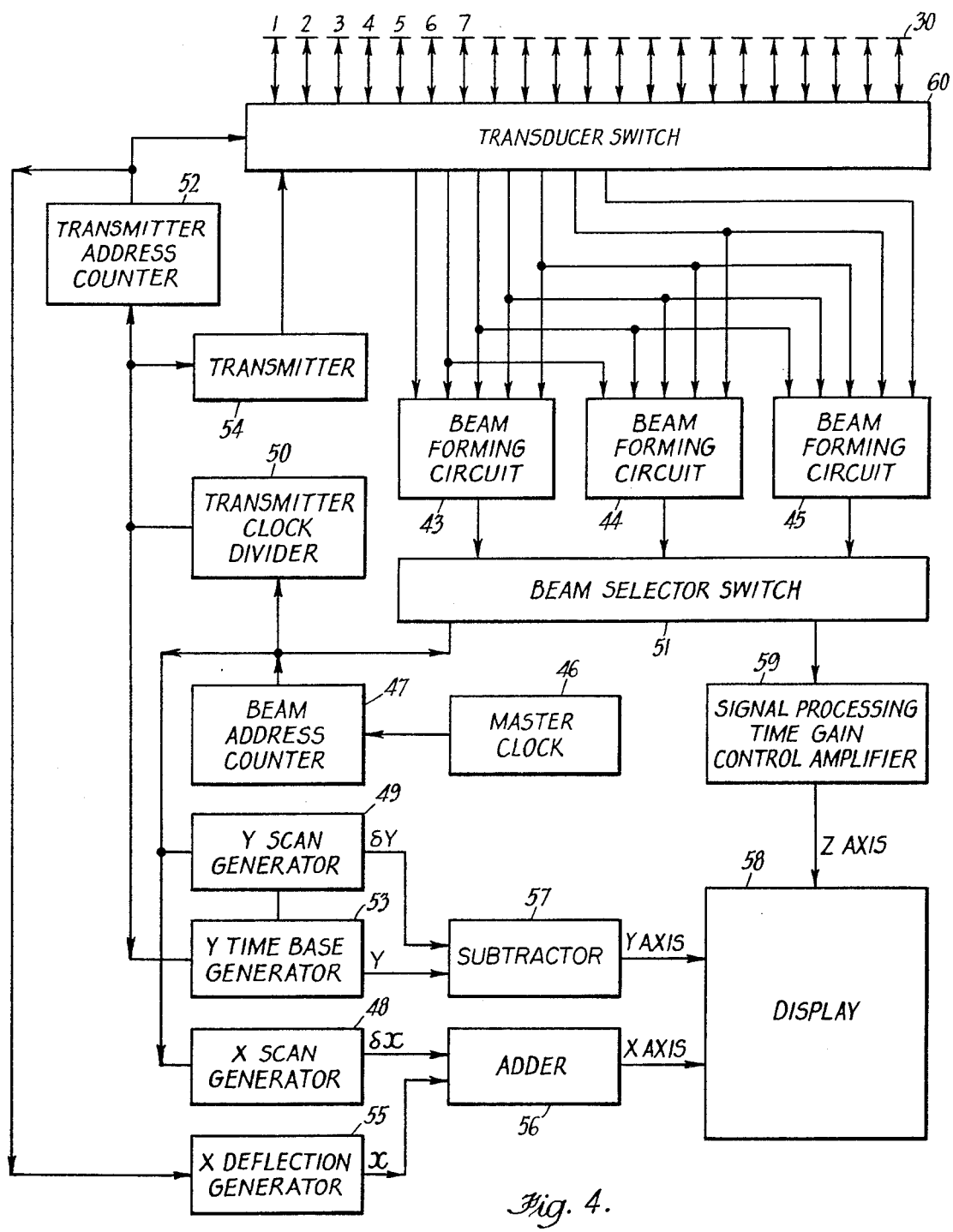
FIG. 4 illustrates the incorporation of the arrangement of elements according to the present invention into an ultrasonic examination system.

An ultrasonic examination system incorporating this invention is shown in FIG. 4. In this system, timing is derived from the main clock 46 which is the most rapid timing interval in the system. A sample is taken from one of the received beams for each pulse of the main clock. The received beam to be used is selected by the beam address counter 47 whose output goes to the beam selector switch 51. The output from the beam address counter 47 also provides information on the value of x for use in the x scan generator 48 and y scan generator 49. The master clock signal 46 is divided down by transmitter clock divider 50 and used to trigger the transmitter address counter 52 and the y time base generator 53. The transmitter address counter 52 output is fed to the transducer switch 60 which selects the appropriate transducer elements from transducer 30 for transmitting and receiving. The transmitting element is pulsed by transmitter 54 and receive elements are connected to beam forming circuits 43, 44, 45. The transmitter address counter 52 is also fed to the x deflection generator 55, the output x of which is added to the output δx of X scan generator 48 in adder 56 and fed to the X deflection of the display 58. The output y of the Y time base 53 is combined with the output of the beam address counter 47 in Y scan generator 49 according to the formula $$\delta y = (\delta x^2/4y)$$

and the output δy of Y scan generator 49 combined with the output y of Y time base generator 53 in subtractor 57 and fed into the Y deflection of the display 58. is as well known in the current art and processes the signals from the beam selector switch 51 for the Z axis input of display 58.

The method may be modified in detail to optimise its performance. For instance a plurality of transducer elements may be employed on transmission to control the amount of divergence of the transmitted beam. The beam forming circuits 43,44,45 etc., may include adding circuits and delay circuits to shape the received beam patterns. Such circuits are well known and reference is made to U.S. Pat. No. 3,166,731 to Joy and No. 3,086,195 to Halliday which disclose electronic steering, focusing and reception of ultrasonics beams.

The method may also be extended in a straight forward fashion to operate on a three-dimensional basis, rather than two-dimensionally as herein described. In this extension it is necessary to have a two-dimensional array of transducer elements and to receive along many lines of sight both within the plane of section before described and also in adjacent planes. In this case means are required to store the information from adjacent planes for subsequent display.

I claim:

1. Apparatus for the ultrasonic examination of an object comprising:
    a linear array of discrete transducer elements;
    means to energize at least one element of said array to transmit a pulse of ultrasonic energy into the object in the form of a diverging beam of transmitted energy which ensonifies a region within the object;
    means for receiving echoes of said pulse of ultrasonic energy reflected by acoustic impedance discontinuities within a respective region of predetermined width and depth of the object, said means for receiving echoes comprising means to activate a plurality of said transducer elements to receive echoes of the transmitted pulse along a plurality of substantially parallel received beams;
    means for sampling said received echoes from said plurality of received beams after a substantially constant time delay relative to the time of transmission of said ultrasonic energy to thereby form a line of image data, said sampling means repeating the sampling at a plurality of substantially constant delay times to produce an output of image lines related to echoes returning from a region of predetermined width and depth within the test object; and
    means for substantially concurrently displaying, the output of said sampling means, including means for displaying said image lines as curves or loci, each curve or locus defining points within the object which serve as a source of said echoes, such that information representative of the acoustic impedance discontinuities within said region is displayed with the time period following the transmission of a single pulse and preceding the transmission of the next pulse.

2. Apparatus as claimed in claim 1, wherein said means for receiving echoes comprises a plurality of said transducer elements arranged to provide a plurality of received beams with beam axes corresponding to each position required for a line of information on a resulting cross-sectional visualisation of the object and
    said means for transmitting a pulse comprises a number of said transducer elements less in number than the number of received beams and arranged to provide said diverging beam of transmitted energy to ensonify the region within the object covered by the plurality of received beams.

3. Apparatus as claimed in claim 1 wherein said means for transmitting a pulse comprises a single element of said array and said means for receiving echoes comprises a plurality of groups of elements of said array providing said plurality of received beams, and further including means for repeatedly sampling the echo information of each of said received beams during the period while echoes are being received.

4. Apparatus as claimed in claim 1 wherein said means for transmitting a pulse comprises a plurality of said transducer elements.

5. Apparatus as claimed in claim 3 wherein said transducer elements of said linear array are of rectangular shape.

6. Apparatus as claimed in claim 3 wherein said linear array of transducer elements is a planar array.

7. A method of ultrasonic examination of an object comprising the steps of:

transmitting a pulse of ultrasonic energy into the object by energizing at least one element of a linear array of discrete transducer elements to form a diverging beam of transmitted energy which ensonifies a region within the object;

receiving echoes of said pulse of ultrasonic energy reflected by acoustic impedance discontinuities within a respective region of predetermined width and depth of the object by activating a plurality of said transducer elements to receive echoes of said transmitted pulse along a plurality of substantially parallel received beams; producing an output of image lines related to echoes returning from a region of predetermined width and depth within the test object; and substantially concurrently displaying, said image lines as curves or loci, each curve or locus defining points within the object which serve as a source of said echoes such that information representative of the acoustic impedance discontinuities within said region is displayed within the time period following the transmission of a single pulse and preceding the transmission of the next pulse.

* * * * *